US00PP34467P2

(12) United States Plant Patent
Bourne

(10) Patent No.: US PP34,467 P2
(45) Date of Patent: Aug. 2, 2022

(54) GRAPEVINE NAMED 'SV33-121-42'

(50) Latin Name: *Vitis vinifera*
Varietal Denomination: 'SV33-121-42'

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 17/803,138

(22) Filed: Mar. 1, 2022

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Eric C. Cole; Baker Manock & Jensen, PC

(57) ABSTRACT

A new and distinct variety of grapevine plant named 'SV33-121-42' particularly characterized by its outstanding muscat flavor and bright red berries which ripen in early July in the McFarland, Calif. area.

2 Drawing Sheets

Latin name of the genus and species of the plant claimed: The plant claimed relates to a new and distinct variety of *Vitis vinifera*.

Variety denomination: The plant claimed shall be known as 'SV33-121-42'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV33-121-42'. As used herein, 'grapevine' refers to all plant parts including, vines, canes, tendrils, leaves, fruit and roots of 'SV33-121-42'. Grapevine named 'SV33-121-42' is the result of an effort to produce an early ripening, red, seedless table grape with fruit characteristics superior to currently available red, seedless cultivar 'Flame Seedless' (unpatented). This new cultivar originated from a cross conducted in May 2012 near McFarland, Calif. between female parent grapevine cultivar 'Sugraone' (U.S. Plant Pat. No. 3,106) and male parent grapevine plant 'SV23-42-380' (unpatented). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in October of 2012 and grown in the greenhouse at 29° C. with 12 hours illumination under high pressure sodium vapor lamps. The seedling population of 93 plants was planted in the field in the spring of 2013 near McFarland, Calif. The new grapevine was selected from this seedling population on Jun. 25, 2014. It was then propagated by cuttings and grafted to 'Freedom' (unpatented) rootstock in 2015. The present invention has been found to retain its distinctive characteristics through two successive asexual propagations.

Grapevine named 'SV33-121-42' differs from the female parent 'Sugraone' (U.S. Plant Pat. No. 3,106) in that grapevine named 'SV33-121-42' has red berries, whereas 'Sugraone' (U.S. Plant Pat. No. 3,106) has green or white berries.

Grapevine named 'SV33-121-42' differs from its male parent 'SV23-42-380' (unpatented) in that grapevine named 'SV33-121-42' has small, crisp berries while 'SV23-42-380' (unpatented) has large, soft textured berries.

Grapevine named 'SV33-121-42' is most similar to commercial cultivar 'Sweet Scarlet' (U.S. Plant Pat. No. 15,891) which also has red berries with muscat flavor. Grapevine named 'SV33-121-42' and 'Sweet Scarlet' (U.S. Plant Pat. No. 15,891) may be distinguished in that grapevine named 'SV33-121-42' ripens in late July when grown in McFarland, Calif. whereas 'Sweet Scarlet' (U.S. Plant Pat. No. 15,891) ripens in late August or early September when grown in the same area. Additionally, grapevine named 'SV33-121-42' produces bunches which average approximately 390 grams whereas 'Sweet Scarlet' (U.S. Plant Pat. No. 15,891) produces bunches which average approximately 1,680 grams.

SUMMARY OF THE INVENTION

The following are the most outstanding and distinguishing characteristics of the ripe fruit of this new variety when grown under normal horticultural practices near McFarland, Calif.:

1. Bright red berries;
2. Very firm berry texture; and
3. Small, sweet berries with a distinct muscat flavor.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 5 years-old, grown in a field near McFarland, Calif. in 2020.

DETAILED BOTANICAL DESCRIPTION

Figure 1:
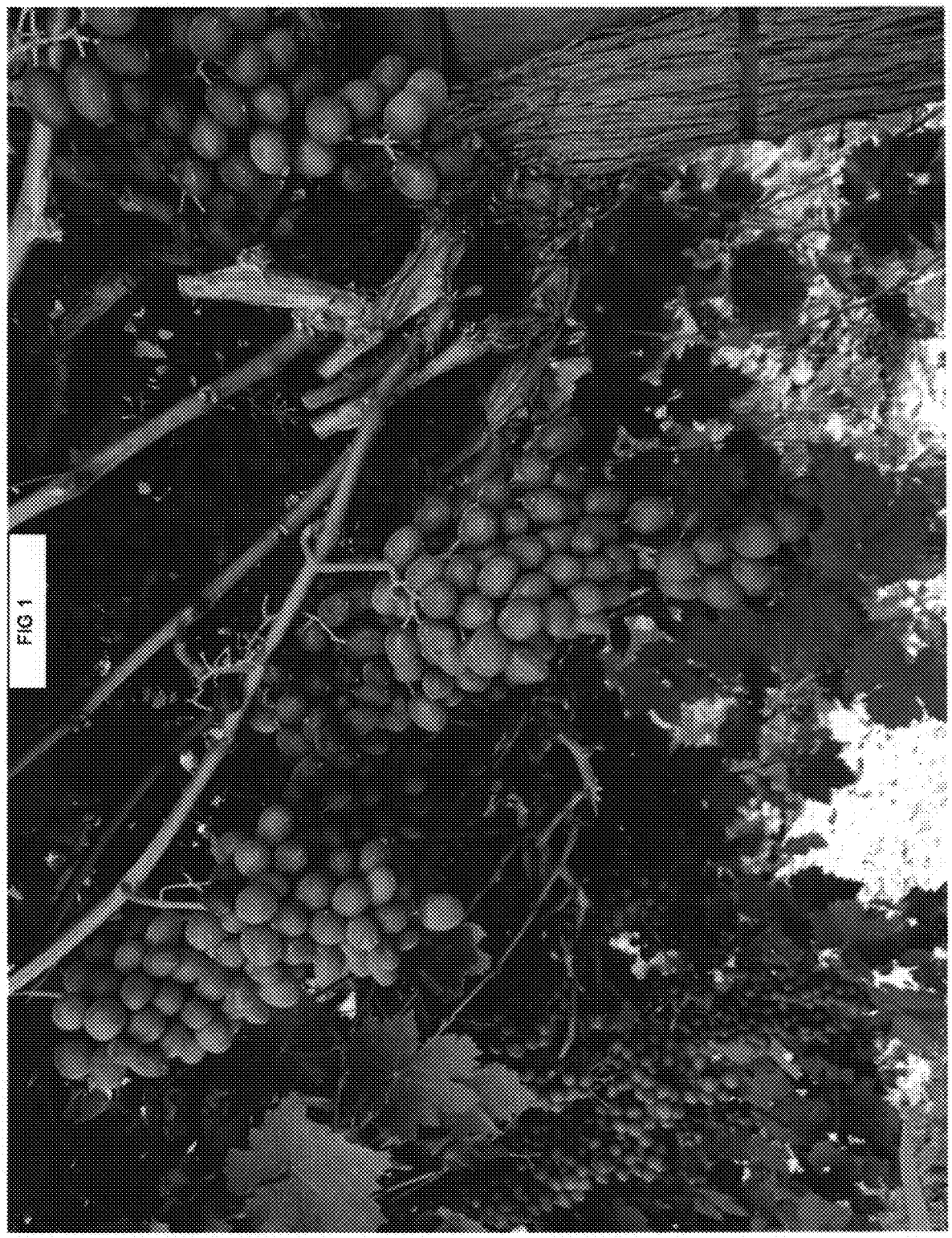
FIG. 1 Vine with clusters treated with exogenous gibberellic acid and trunk girdling.
Figure 2:
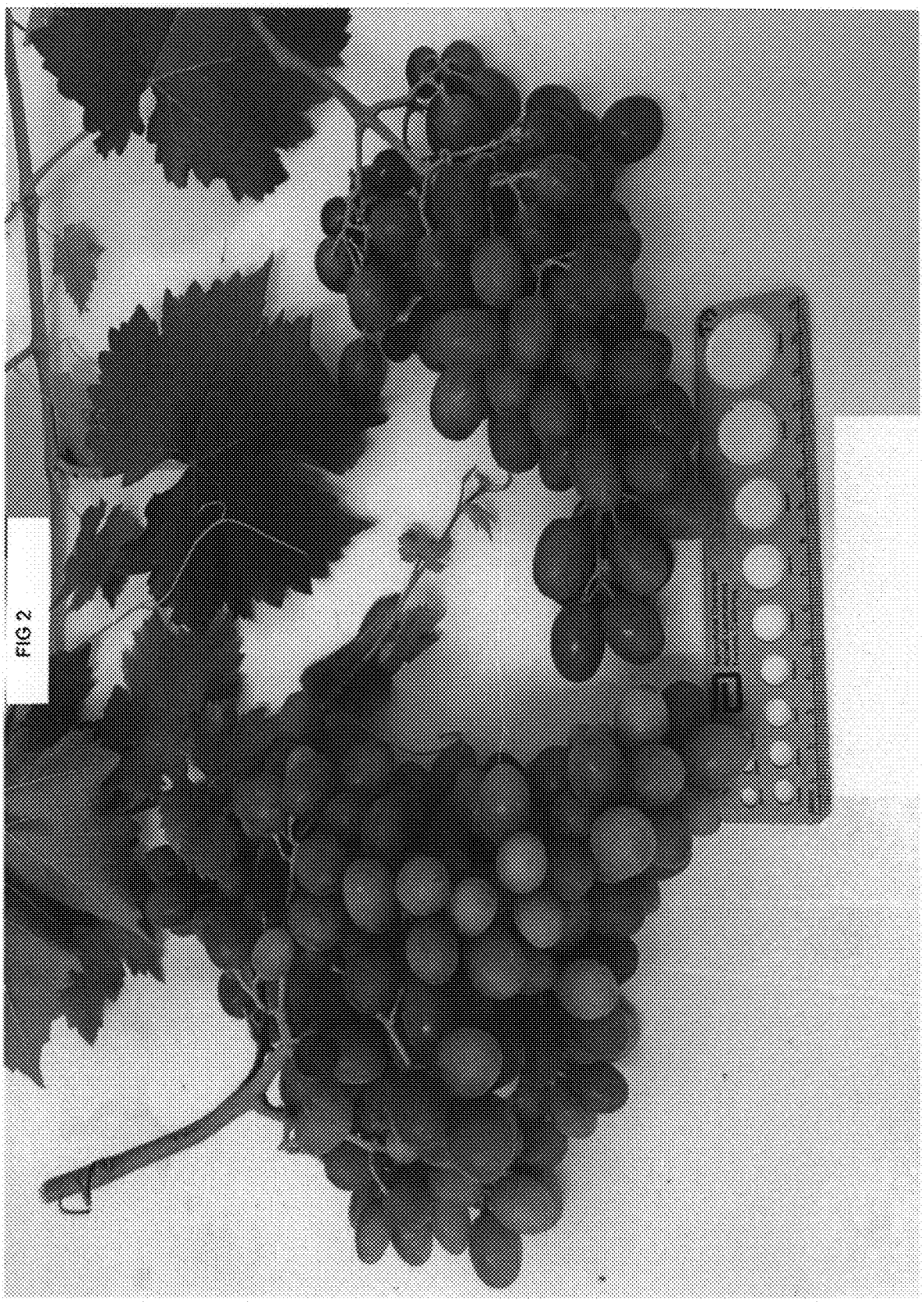
FIG. 2 Fruit cluster natural (at left) and fruit cluster treated with gibberellic acid and trunk girdling (at right) with green shoot bearing leaves and tendrils.

The following detailed description sets forth the distinctive characteristics of grapevine 'SV33-121-42'. Descriptions of the new invention apply to vines of grapevine 'SV33-121-42' grown on 'Freedom' (unpatented) rootstock at a density of 1,537 vines per hectare grown near McFarland, Calif. in 2021. These vines were in their fifth year of full production having been planted in 2016. These descriptions are believed to apply generally to the new variety grown under similar circumstances elsewhere. Variation due to soil and climatic conditions in other locations may be seen. References to color primarily correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV33-121-42'.

Plant:

*Vigor*.—Vigorous: vines spur-pruned and shoot thinned to 32 shoots average 162 cm of growth per cane.

*Density of foliage*.—Dense.

*Training method*.—Spur pruned with 32 two bud shoots per vine.

*Productivity*.—Moderate when spur pruned, up to 14,141 kg/hectare.

*Hardiness*.—Hardiness observed to 0° C. when grown near McFarland, Calif. in USDA hardiness zone 9A.

*Rootstock*.—'Freedom' (unpatented).

Trunk:

*Shape*.—Broadly elliptical.

*Straps*.—Long, split.

*Surface texture*.—Shaggy.

*Trunk circumference*.—27.1 cm at 1.0 m of height.

*Inner bark color*.—Greyed orange group 177C.

*Outer bark color*.—Brown group N200B.

Mature leaves:

*Average blade length*.—17.4 cm.

*Average blade width*.—15.7 cm.

*Size of blade*.—Large.

*Shape*.—Pentagonal.

*Number of lobes*.—5.

*Anthocyanin coloration of main veins on the upper side of the blade*.—Absent.

*Mature leaf profile*.—Cupped upwards around entire margin.

*Blistering* (*upper surface*).—Absent.

*Leaf blade tip*.—Curved upward.

*Margins*.—Lobed, serrated, undulating.

*Apex*.—Broadly acuminate.

*Bases*.—Sagittate.

*Thickness*.—Medium.

*Undulation of blade between main and lateral veins*.—Slight.

*Shape of teeth*.—Broadly conical, both sides convex.

*Length of teeth*.—7.5 mm.

*Ratio length/width of teeth*.—About 1:1.

*General shape of petiole sinus*.—Half open.

*Tooth at petiole sinus*.—Absent.

*Petiole sinus limited by veins*.—Absent.

*Prostrate hairs between veins* (*lower surface*).—Absent.

*Erect hairs between veins* (*lower surface*).—Absent.

*Prostrate hairs on main veins* (*lower surface*).—Present.

*Density of erect hairs on main veins* (*lower surface*).—Sparse.

*Prostrate hairs on main veins* (*upper surface*).—Present though very sparse.

*Upper surface*.—Summer color: Yellow green group 146A. Surface texture: Smooth. Surface appearance: Dull. Goffering of blade: Absent.

*Lower surface*.—Summer color: Yellow green group 146B. Anthocyanin coloration of main veins on lower leaf surface: Absent. Anthocyanin coloration on laterals: Absent. Glossiness: Low. Pubescence: Absent. Surface texture: Rough. Surface appearance: Dull.

*Petiole*.—Length: 12.0 cm. Length of petiole compared to middle vein: Slightly longer. Density of prostrate hairs: Very sparse; limited to junction of petiole and blade. Density of erect hairs: Moderate; limited to the junction of petiole and blade. Shape of base of petiole sinus: Ovate. Color: In shade: Yellow green group 145A with streaks of Red purple group 60D. In sun: Red purple group 59D with some Yellow green group 144C.

Tendrils:

*Number*.—Bifurcated and trifurcated; forming irregularly at nodes above node 5.

*Length*.—19.1 cm.

*Diameter*.—3 mm.

*Texture*.—Smooth.

*Color*.—Yellow green group N144C, with streaks of Red purple group 61A.

Growing tips (young shoot):

*Pubescence*.—Abundant, prostrate.

*Color*.—RHS 144C (yellow green group).

*Anthocyanins*.—Absent.

*Shape*.—Rounded.

*Apex*.—Fully open.

*Shoot attitude*.—Semi-erect.

Green summer shoots:

*Internode color upper surface*.—Yellow green group 144B.

*Internode color lower surface*.—Yellow green group 144A.

*Node color upper surface*.—Yellow green group 144B.

*Node color lower surface*.—Yellow green group 144B.

*Density of erect hairs on internodes*.—Absent.

Woody shoot:

*Canes*.—Shape, cross section: Elliptic Internode length: 11.4 cm. Width at node: 10.2 mm. Cross section at node: Elliptic. Surface: Smooth. Main color: Greyed orange group 167A. Lenticels: Inconspicuous.

*Buds*.—Shape: Conical. Cane bud fruitfulness: Fruitful from 2 basal buds 1 and 2. Length: 7 mm. Width: 6 mm. Height: 6 mm. Color: Greyed orange group 175A. Texture: Smooth.

Flowers:

*Flower sex*.—Hermaphrodite.

*Position of first flowering nodes*.—Third or fourth.

*Number of inflorescences per shoot*.—2.

*Flower cluster width*.—4.9 cm.

*Flower cluster length* (*including peduncle*).—20.9 cm.

*Cluster stem color*.—Yellow green group 144A.

*Calyptra color*.—Yellow green group 144A.

*Ovary length*.—3 mm.

*Ovary width*.—1 mm.

*Ovary color*.—Yellow green group 144B.

*Filament length*.—2 mm.

*Filament color*.—Translucent, absence of pigmentation.

*Anther length*.—1 mm.

*Anther color*.—Yellow group 8B.

*Date of full bloom*.—May 8th.

Fruit:

*Ripening period*.—Early summer in McFarland, Calif.

*Date of first harvest*.—July 8$^{th}$, McFarland, Calif.

*Use*.—Fresh market.

*Keeping quality*.—Very good.

*Shipping quality*.—Good.

*Solids-sugar*.—18.5 brix at full maturity.

*Refractometer test*.—18.5 brix.

*Titratable acidity of juice*.—0.59.

*PH of juice*.—3.55.

*Bunch*.—Size: Small. Length (peduncle excluded): About 18.5 cm. Width: About 11.4 cm. Weight: Natural, without gibberellic acid treatment: 295 g. With gibberellic acid treatment: 290 g. Density: Well-filled to compact. Number of berries per cluster: 82.4 Form: Pyramidal.

*Peduncle*.—Length: About 6.0 cm. Lignification: Peduncle not lignified at maturity. Color: Yellow green group 114B.

*Berry*.—Size: Small. Uniformity of size: Uniform. Weight: Natural, without gibberellic acid treatment: 3.3 g. With gibberellic acid treatment: 3.5 g. Shape: Natural, without gibberellic acid treatment: Elliptic. With gibberellic acid treatment: Elliptic. Presence of seeds: Seedless; most berries develop one or two small, soft. rudimentary seeds 0.5 mm in length. Cross section: Circular. Dimensions: Longitudinal axis: 2.3 cm. Horizontal axis: 1.9 cm. Skin color (without bloom): Red group 53A. Coloration of flesh: Translucent; no pigment. Juiciness of flesh: Juicy. Berry firmness: Very firm. Particular flavor: Distinct muscat flavor. Bloom (cuticular wax): Medium. Pedicel length: 1.3 cm. Berry separation from pedicel: Moderately easy.

*Skin*.—Thickness: Medium. Texture: Crisp. Reticulation: Absent. Roughness: Smooth. Tenacity: Tenacious to flesh. Tendency to crack: Resistant.

Disease and insect resistance: No particular resistance or susceptibility has been observed to pests of roots, shoots, leaves or fruit. Normal disease control practices typically used under central California conditions may be used.

Having thus described and illustrated our new variety of grapevine, we claim:

1. A new and distinct variety of grapevine plant named 'SV33-121-42', substantially as illustrated and described herein.

* * * * *